US00PP36331P2

(12) United States Plant Patent
Noland

(10) Patent No.: US PP36,331 P2
(45) Date of Patent: Dec. 24, 2024

(54) KIWI PLANT NAMED 'W11'

(50) Latin Name: *Actinidia chinensis*
Varietal Denomination: W11

(71) Applicant: Wild River Marketing, Inc., Marysville, CA (US)

(72) Inventor: Michael Gordon Noland, Penn Valley, CA (US)

(73) Assignee: Wild River Marketing, Inc., Marysville, CA (US)

( * ) Notice: Subject to any disclaimer, the term of this patent is extended or adjusted under 35 U.S.C. 154(b) by 0 days.

(21) Appl. No.: 18/410,676

(22) Filed: Jan. 11, 2024

(51) Int. Cl.
*A01H 5/08* (2018.01)
*A01H 6/00* (2018.01)

(52) U.S. Cl.
USPC ..... Plt./156

(58) Field of Classification Search
USPC ..... Plt./156
See application file for complete search history.

(56) References Cited

U.S. PATENT DOCUMENTS

PP11,066 P 9/1999 Lowe et al.
PP22,159 P3 9/2011 Dozier, Jr. et al.
PP22,191 P2 10/2011 Dozier, Jr. et al.

*Primary Examiner* — Karen M Redden
*Assistant Examiner* — Zachariah Allan Kay
(74) *Attorney, Agent, or Firm* — Morrison & Foerster LLP

(57) ABSTRACT

A new and distinct variety of kiwi plant named 'W11', particularly selected for its superior flavor, consistent yellow color, limited thinning requirements, advantageous market timing, and long storage while retaining high quality, is disclosed.

16 Drawing Sheets

Latin name:
Botanical classification: *Actinidia chinensis.*
Varietal denomination: The varietal denomination of the claimed variety of kiwi plant is 'W11'.

BACKGROUND OF THE INVENTION

Kiwis, also known as kiwifruit or Chinese gooseberries, are shrubs or woody vines of the genus *Actinidia* grown for their edible fruit. The genus *Actinidia* includes approximately 50 species native to temperate East Asia. *Actinidia deliciosa* was first cultivated outside of China in New Zealand, beginning in the early 20$^{th}$ century, and is the most commercially important kiwi species. The golden kiwi, *A. chinensis*, is also grown commercially as a fruit crop. Other species like *A. arguta* are grown on a limited scale for their fruits.

Kiwi plants are cultivated in warm temperate climates, typically on trellises or other support structures. Kiwi cultivation and training requirements are generally similar to grapevines. *Actinidia* are usually dioecious. Male plants produce staminate flowers, while female plants produce flowers with sterile anthers. Thus, kiwi production requires interplanting male pollinizer varieties and the presence of a pollen vector (typically honeybees) for proper fruit set. Commercial kiwi production relies on grafting to produce the proper ratio of female and male plants. Designated rootstock varieties may be used, but rootstocks are often seedlings of open-pollinated commercial kiwi varieties. 'Hayward', an *A. deliciosa* variety selected soon after that species' introduction in New Zealand, remains the most commercially important female kiwi variety.

Kiwi fruits are appreciated for their vibrant green or yellow flesh color, tart flavor, and the contrasting texture between soft, juicy flesh and crunchy, edible seeds. Kiwis are usually consumed fresh after removing the skin, which is edible but hirsute in *A. deliciosa* and *A. chinensis.*

Kiwi is an important and valuable fruit crop. Accordingly, there is a need for new varieties of kiwi plants. In particular, there is a need for improved varieties of kiwi plant that are stable, high yielding, and agronomically sound.

SUMMARY OF THE INVENTION

In order to meet these needs, the present invention is directed to an improved variety of kiwi plant. In particular, the invention relates to a new and distinct variety of kiwi (*Actinidia chinensis*) plant, which has been denominated as 'W11'.

Kiwi plant variety 'W11' was discovered in Marysville, California in 2018, in a cultivated field, and selected from a population of kiwi plants. The parentage of this variety is unknown. 'W11' was identified in a screen for kiwi plants with desirable qualities from among the population of kiwis. The original plant of 'W11' was first asexually propagated via grafting scions onto rootstocks in 2019. The selection reproduces asexually and stays true to type.

Subsequent asexual propagation of 'W11' was conducted by grafting scions onto rootstock. 'W11' has undergone testing in Marysville, California for one year (2022 to 2023). 'W11' has been found to be stable and reproduce true to type through successive generations of asexual propagations via grafting onto rootstock. Specifically, 'W11' is grown on rootstock of kiwi variety 'Bruno' (not patented). 'W11' can be pollinated with pollen from both *Actinidia deliciosa* and *Actinidia chinensis* species.

'W11' was particularly selected for superior flavor; consistent yellow color; reduced thinning requirements as the variety exhibits a high percentage of single, ideally formed buds; and later harvest and longer high-quality storage (over 5 months under optimal storage conditions), which enables growers to ship fruit during windows in which other *A. chinensis* varieties may no longer be in the market.

BRIEF DESCRIPTION OF THE DRAWINGS

This new kiwi plant variety is illustrated by the accompanying photographs. The colors shown are as true as can be reasonably obtained by conventional photographic procedures. The photographs are of plants that are 4-5 years old, unless otherwise specified.

FIG. 2A illustrates Spring budbreak on a 1-year old shoot of 'W11'. FIG. 2B illustrates floral buds on a new shoot and lenticel patterning on a 1-year-old-shoot of 'W11'.

FIG. 3A illustrates the upper leaf surface of a 'W11' leaf basal from the stem. FIG. 3B illustrates the lower leaf surface of a 'W11' leaf basal from the stem. FIG. 3C illustrates the upper (right) and lower (left) leaf surface of 'W11' leaves distal from the stem.

FIG. 4A illustrates a shoot with multiple flowers of 'W11'. FIG. 4B illustrates a closer image of the flowers of 'W11', including the upper flower surface (foreground) and the lower flower surface (background).

FIG. 5A illustrates many developing, immature fruit on the vine of 'W11'. FIG. 5B illustrates a closer image of several developing, immature fruit on the vine of 'W11'. FIG. 5C illustrates a single mature fruit of 'W11' (foreground), along with the lenticel patterning of the shoot. FIG. 5D illustrates a group of mature fruit on the vine of 'W11'.

FIG. 6A illustrates four whole 'W11' fruits' stalk ends. FIG. 6B illustrates a longitudinal view of four whole 'W11' fruit. FIG. 6C illustrates a whole 'W11' fruit (center) and longitudinal (left) and transverse (right) fruit sections of 'W11'. FIG. 6D illustrates a closer view of FIG. 6C's longitudinal section. FIG. 6E illustrates a closer view of FIG. 6C's transverse section. FIG. 6F illustrates the stem end (or "stock end") of a whole 'W11' fruit.

DETAILED BOTANICAL DESCRIPTION

Figure 1:
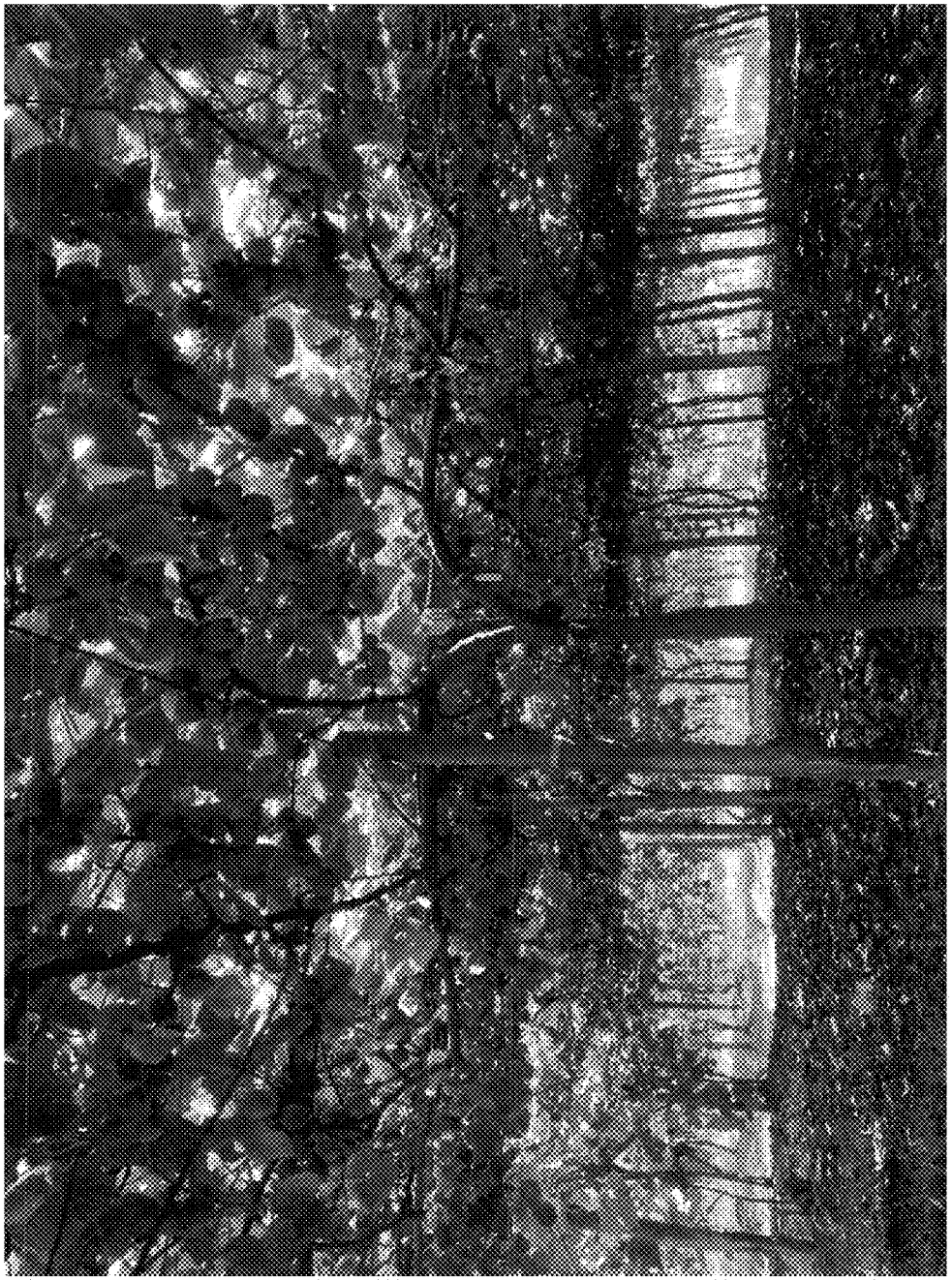
FIG. 1 illustrates one whole plant of 'W11' (foreground, tagged with two neon orange flags) among multiple kiwi plant varieties (background).
Figure 2A:
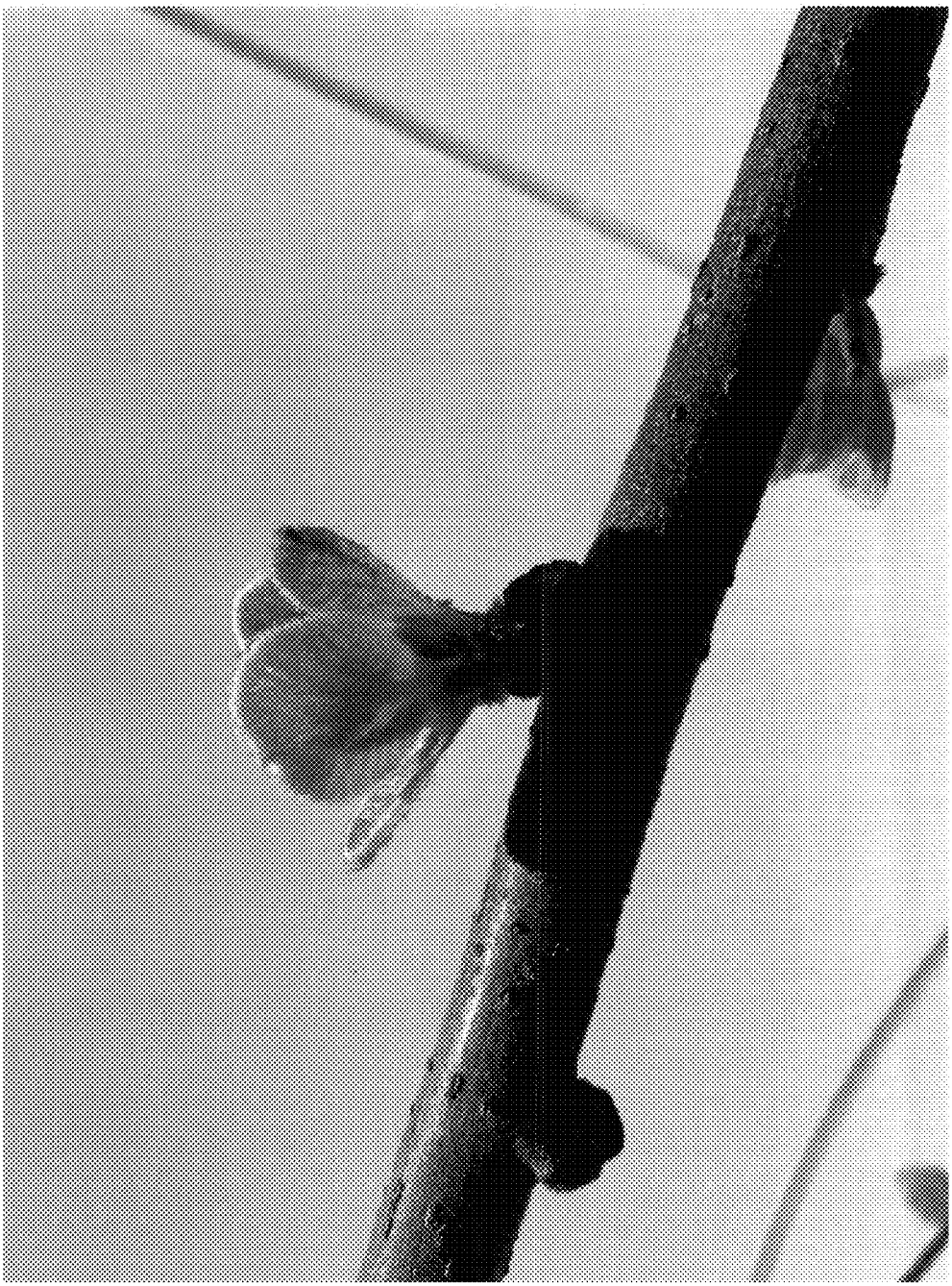
FIGS. 2A-2B illustrate buds on a 1-year-old shoot of 'W11'.
Figure 2B:
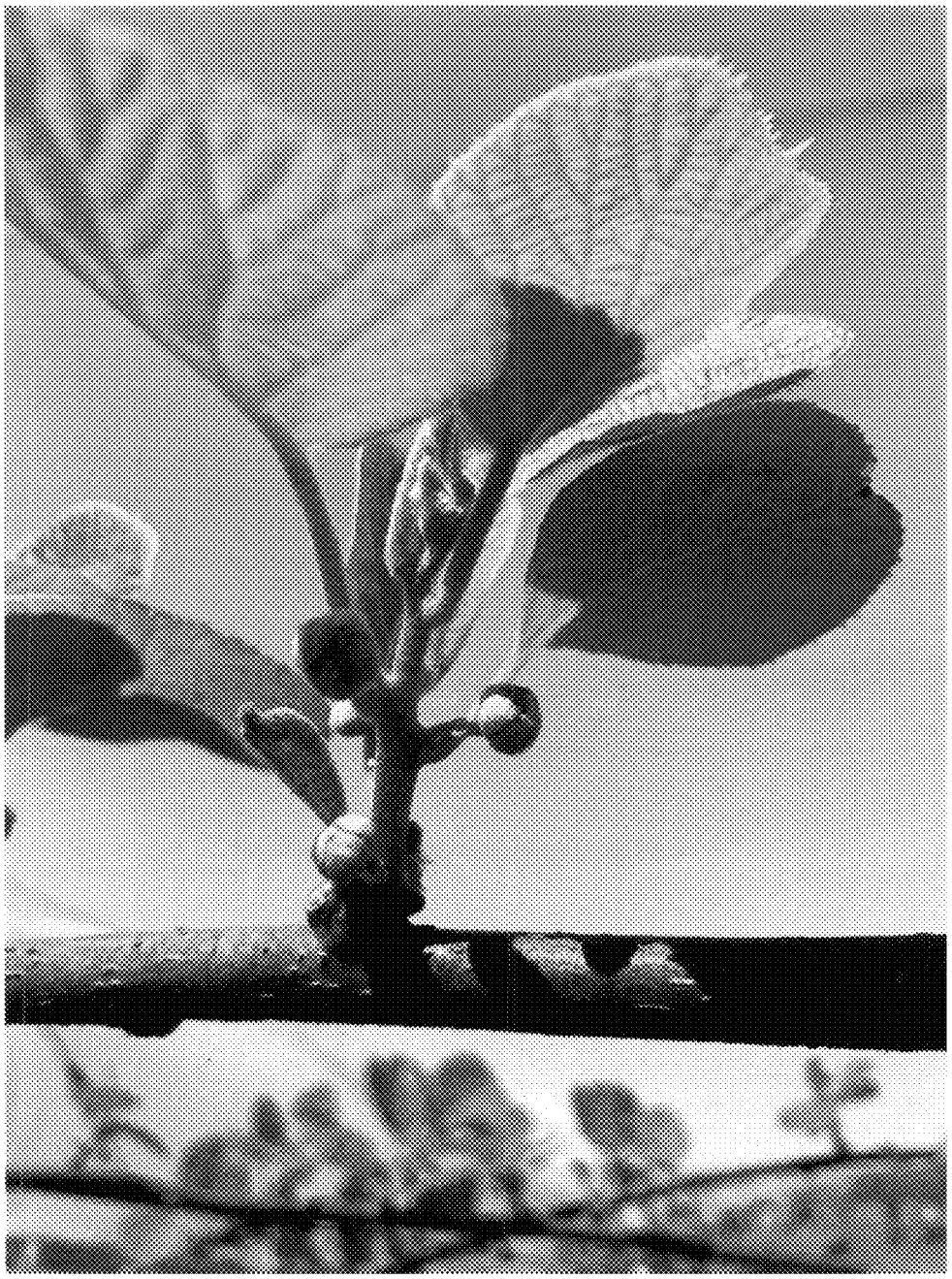
Figure 3B:
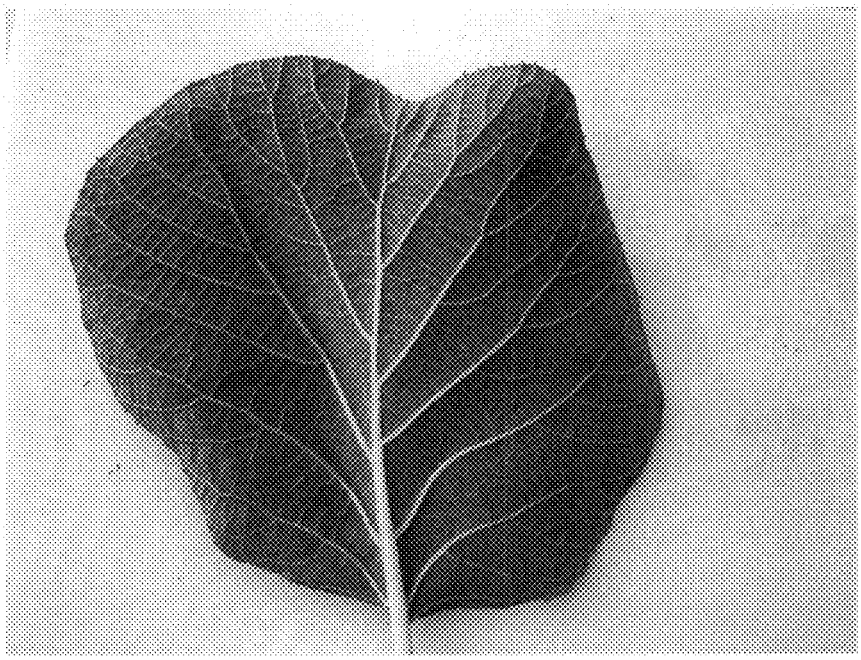
FIGS. 3A-3C illustrate leaves of 'W11'.
Figure 3A:
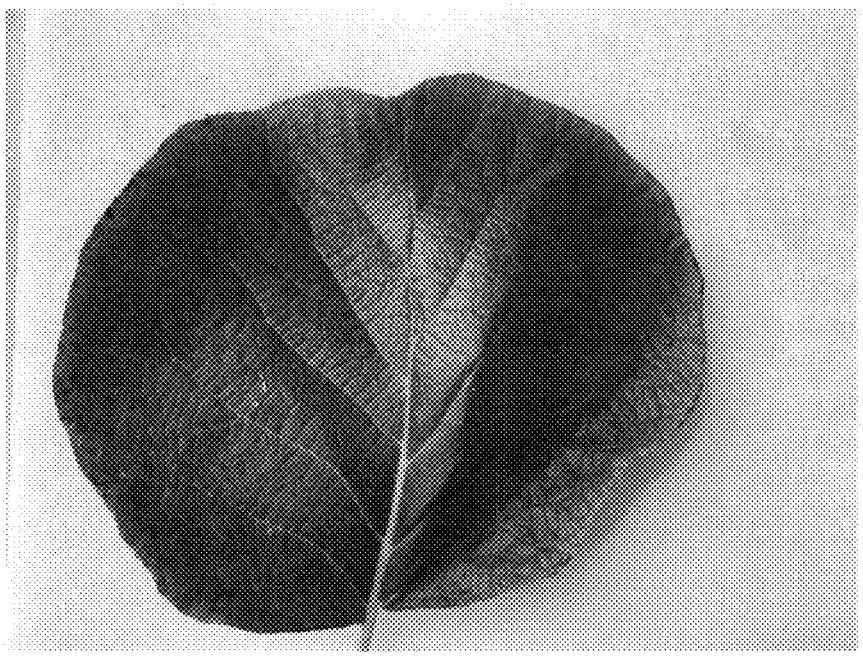
Figure 3C:
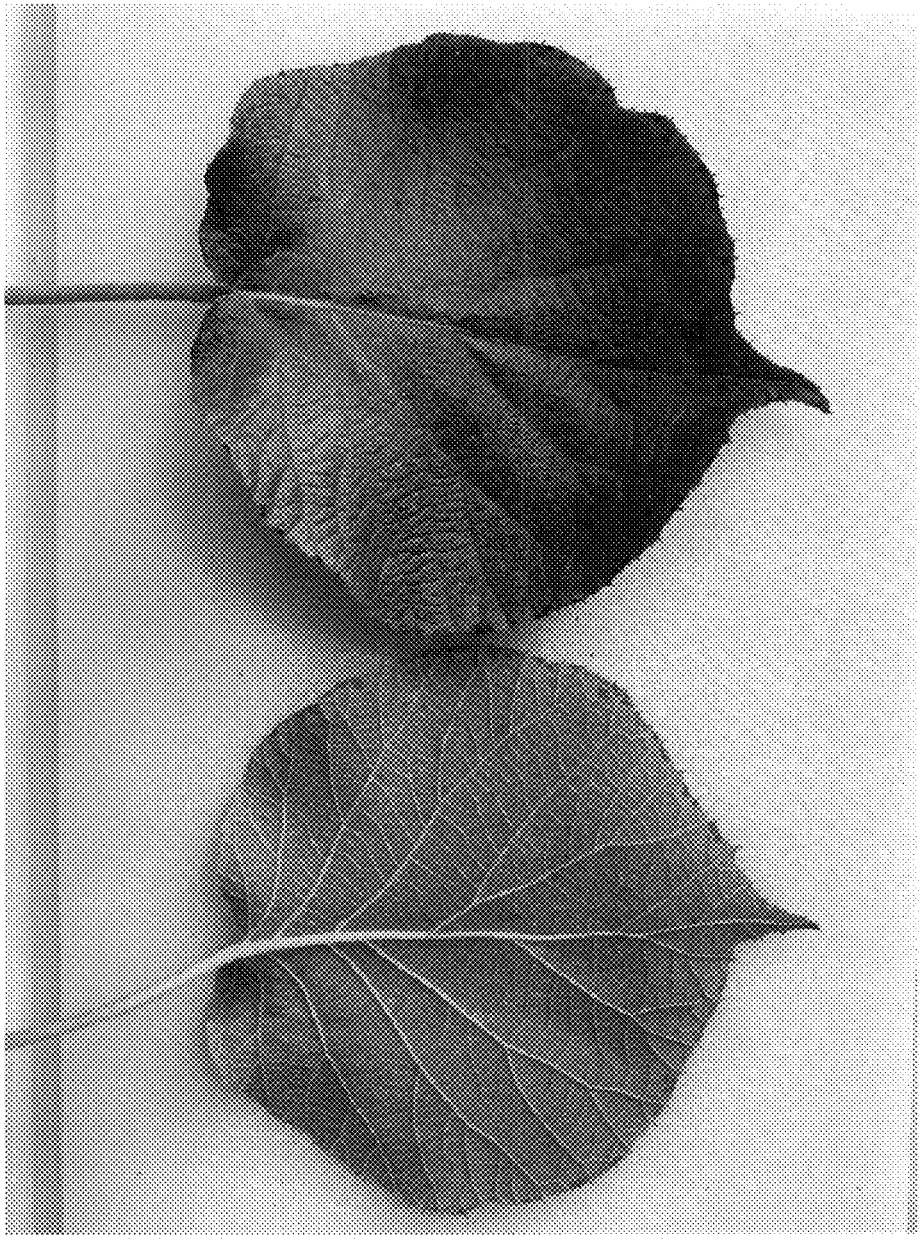
Figure 4A:
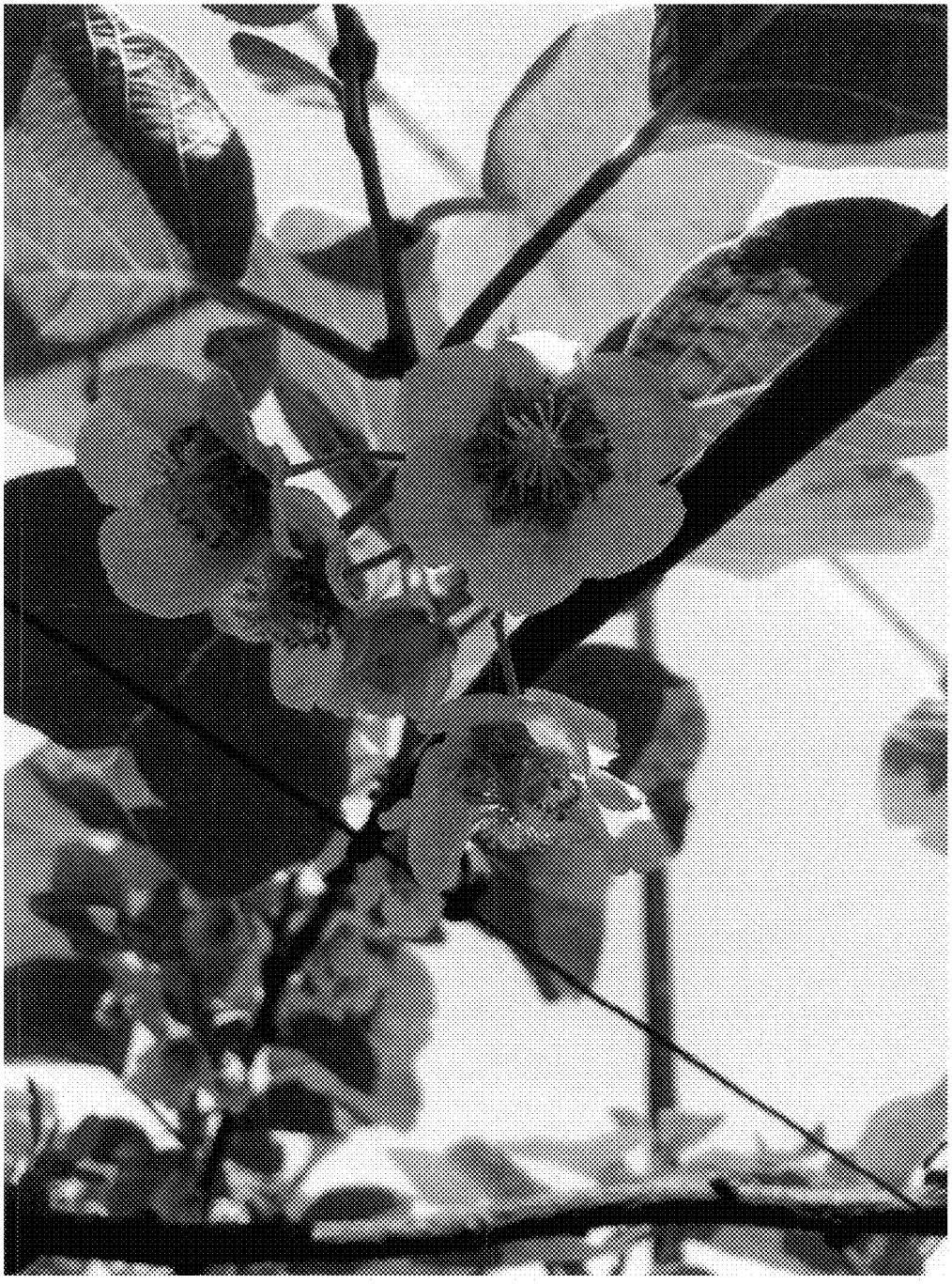
FIGS. 4A-4B illustrate flowers of 'W11'.
Figure 4B:
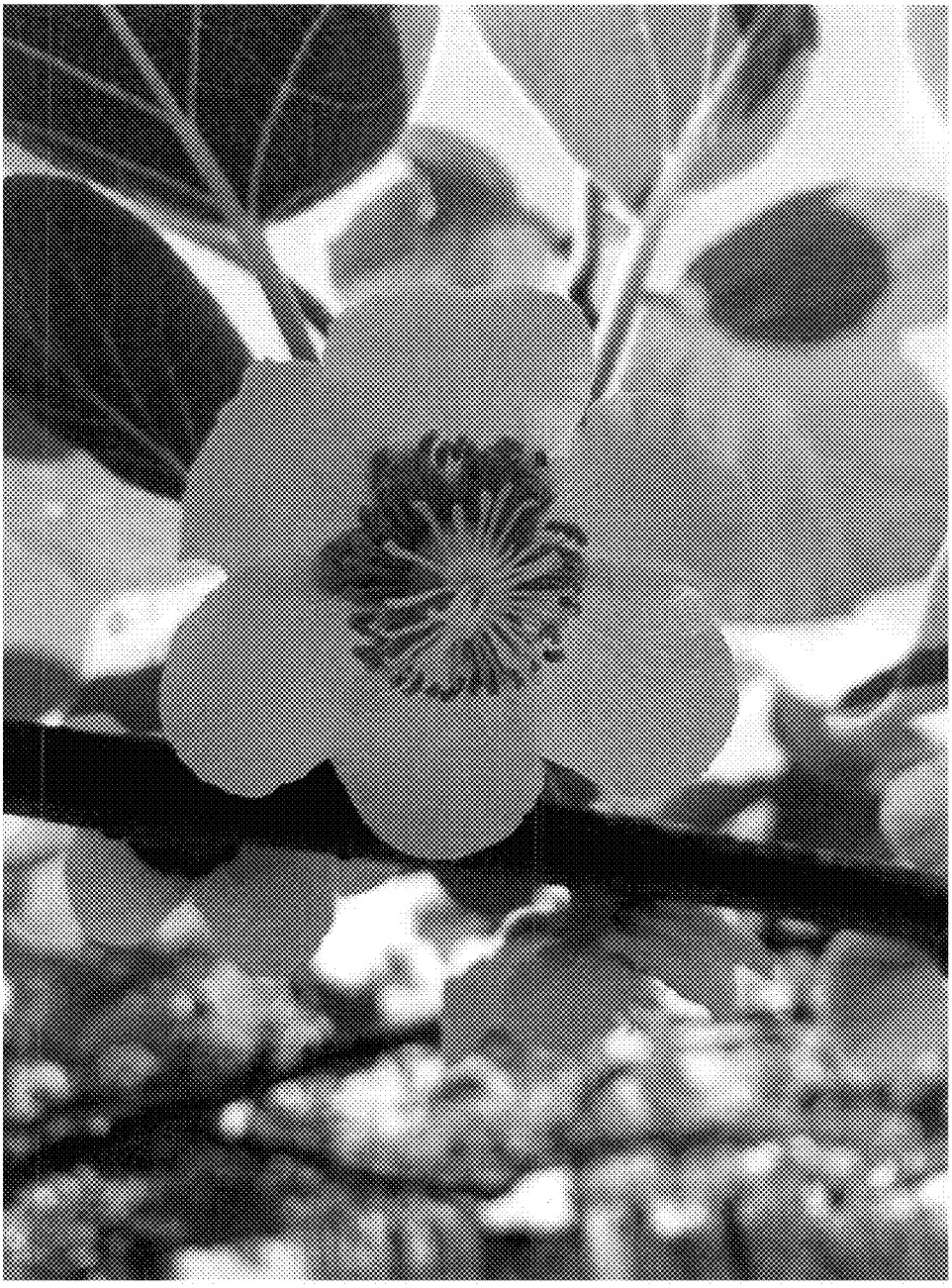
Figure 5A:
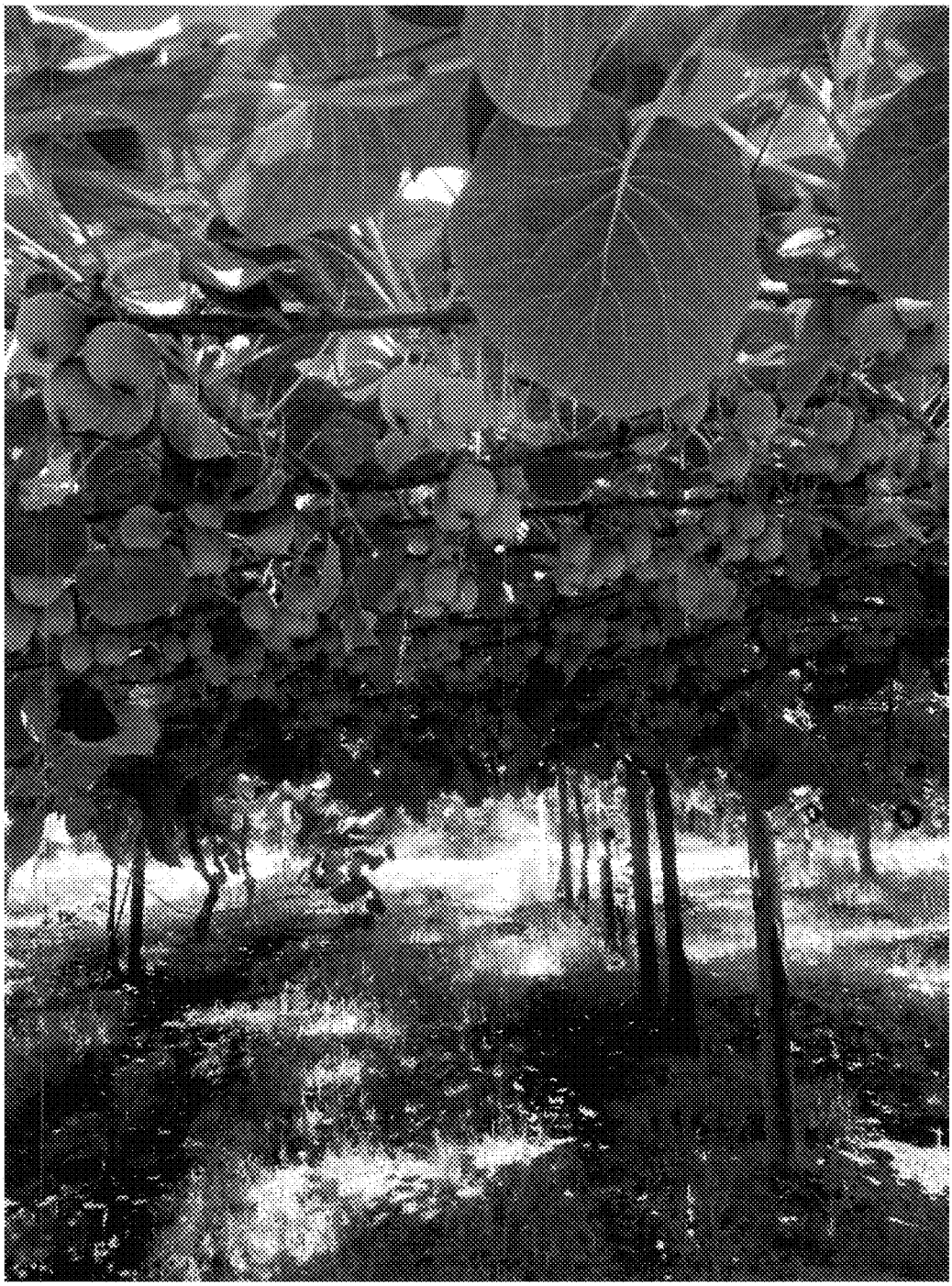
FIGS. 5A-5D illustrate the development of 'W11' fruit.
Figure 5B:
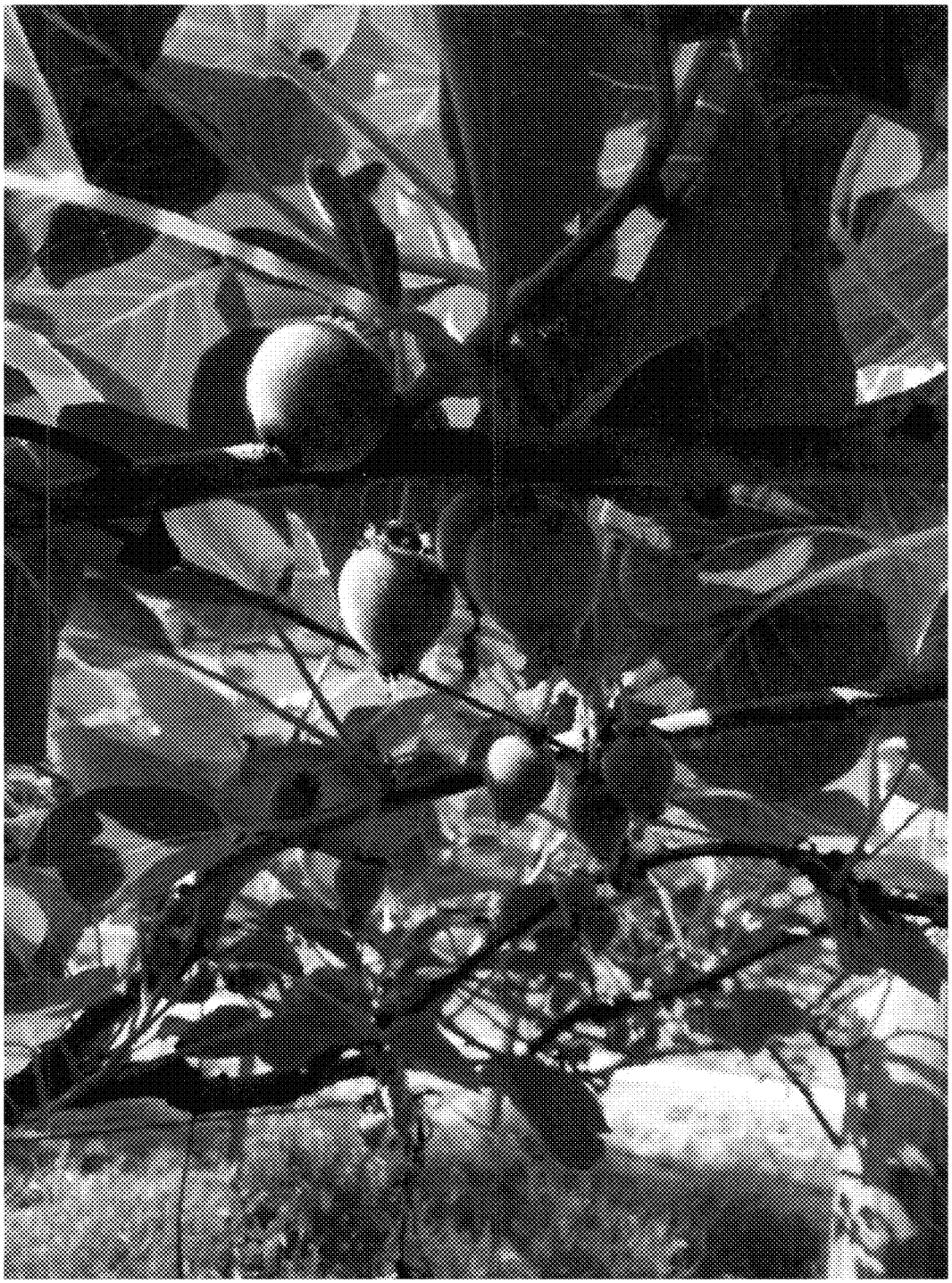
Figure 5C:
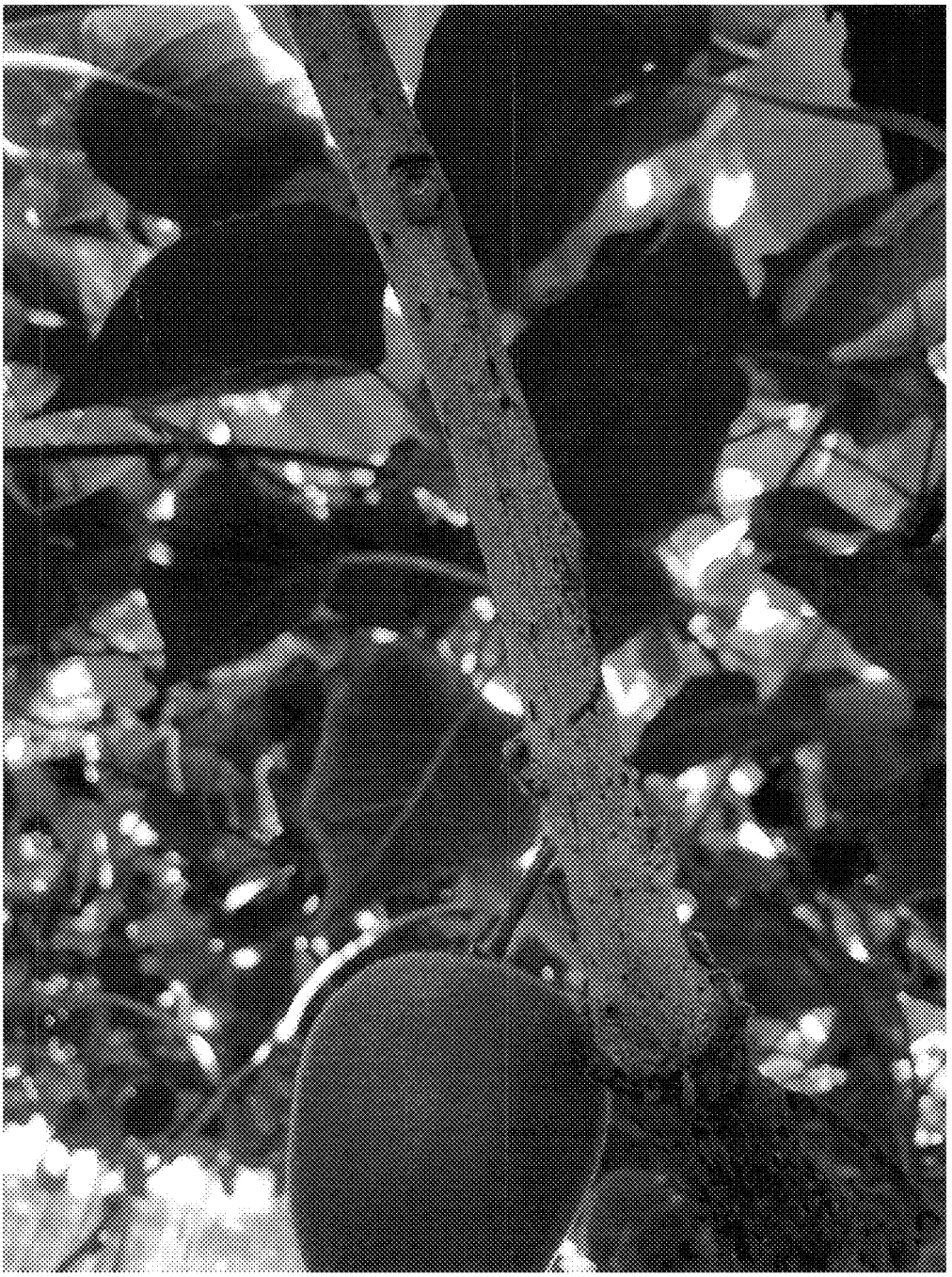
Figure 5D:
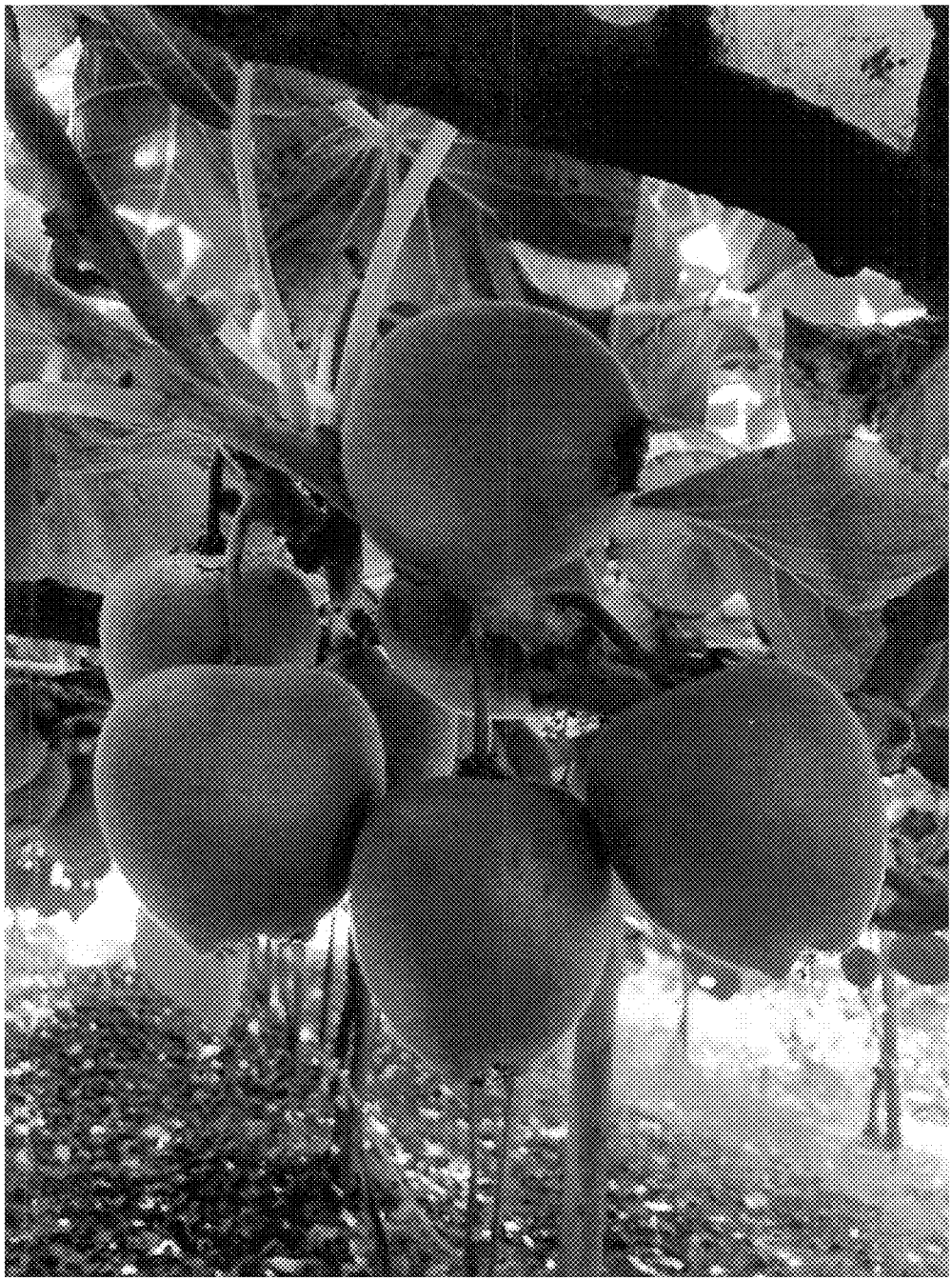
Figure 6A:
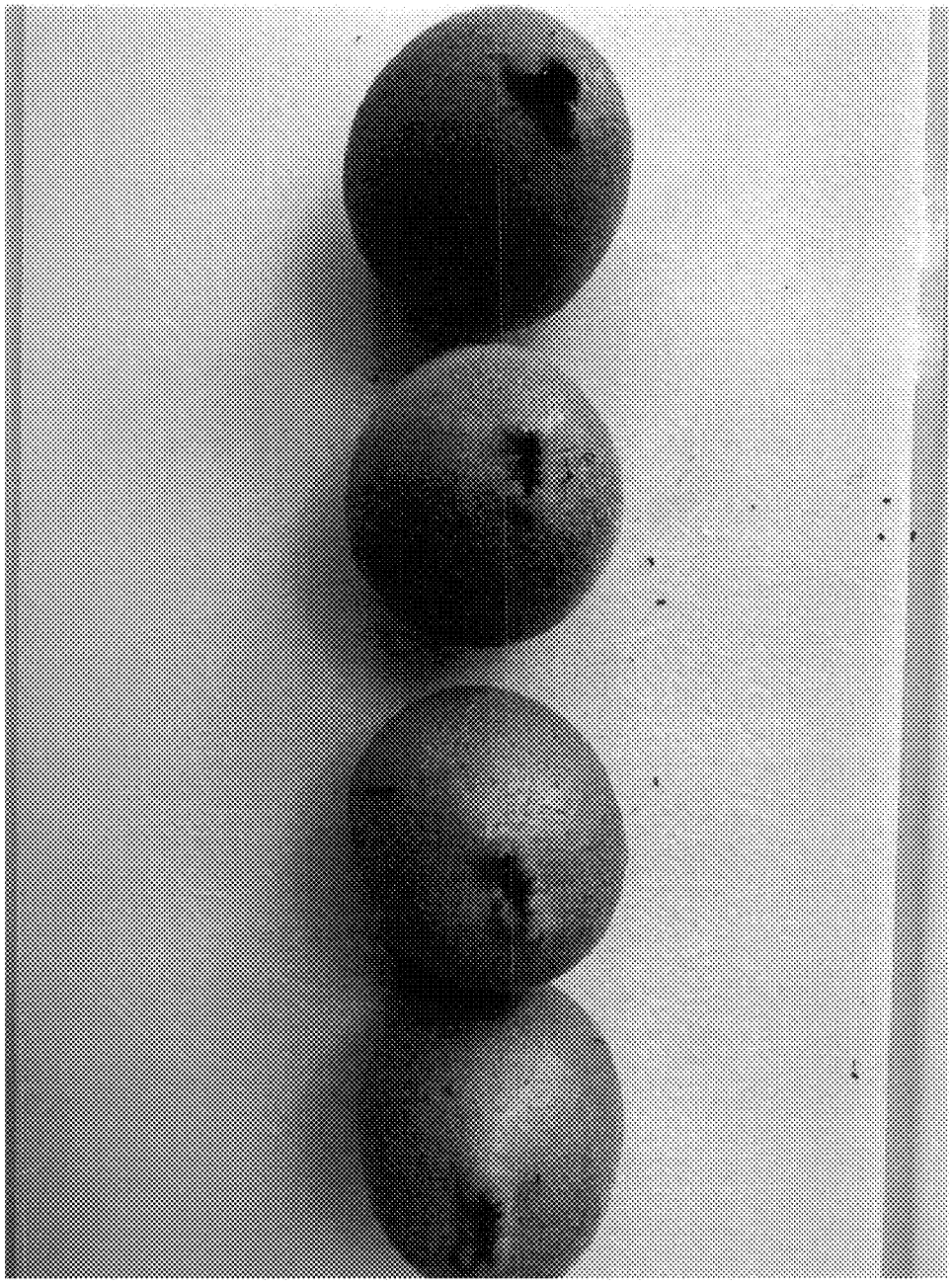
FIGS. 6A-6F illustrate whole fruit and fruit sections of mature 'W11' fruit.
Figure 6B:
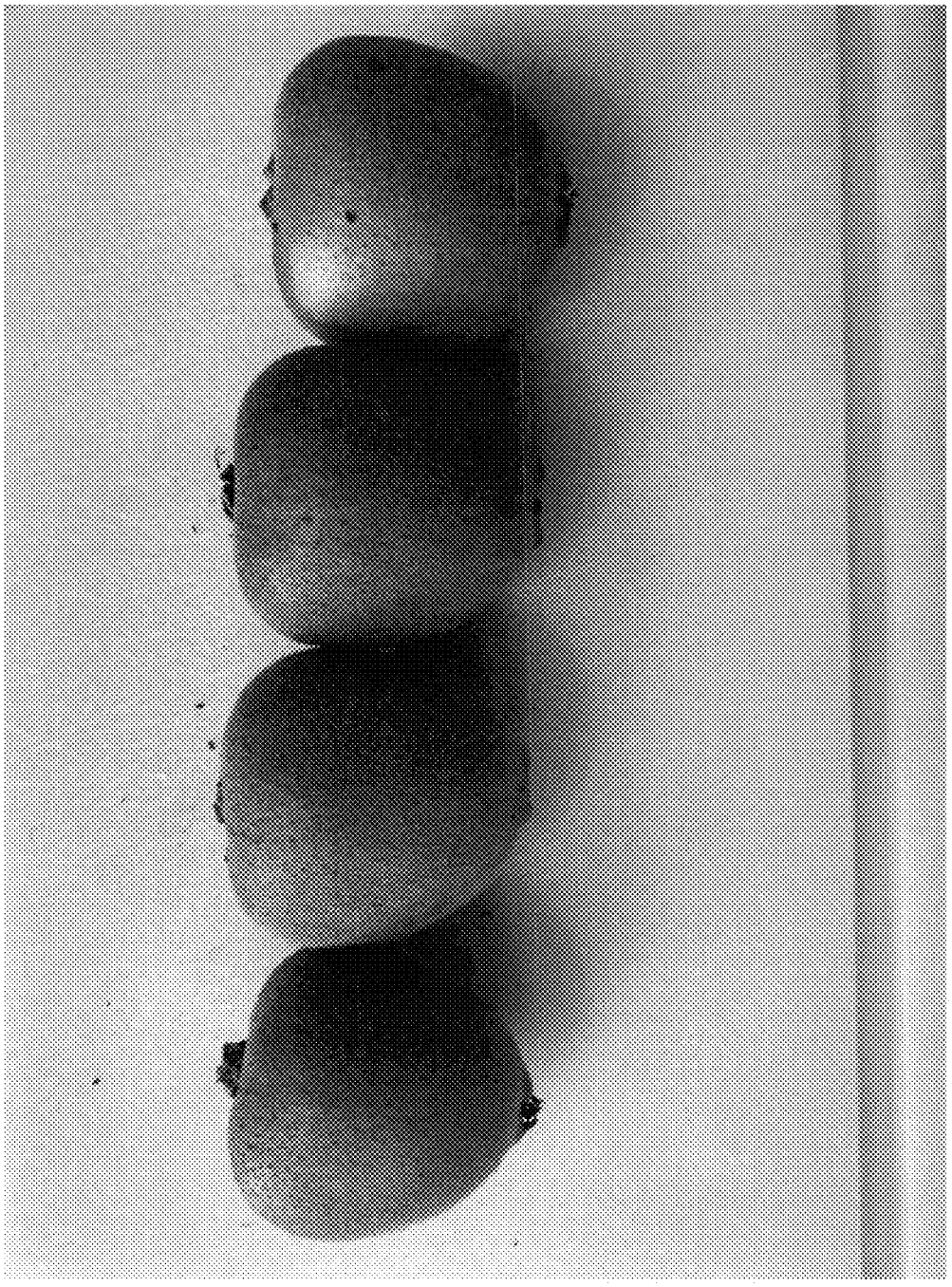
Figure 6C:
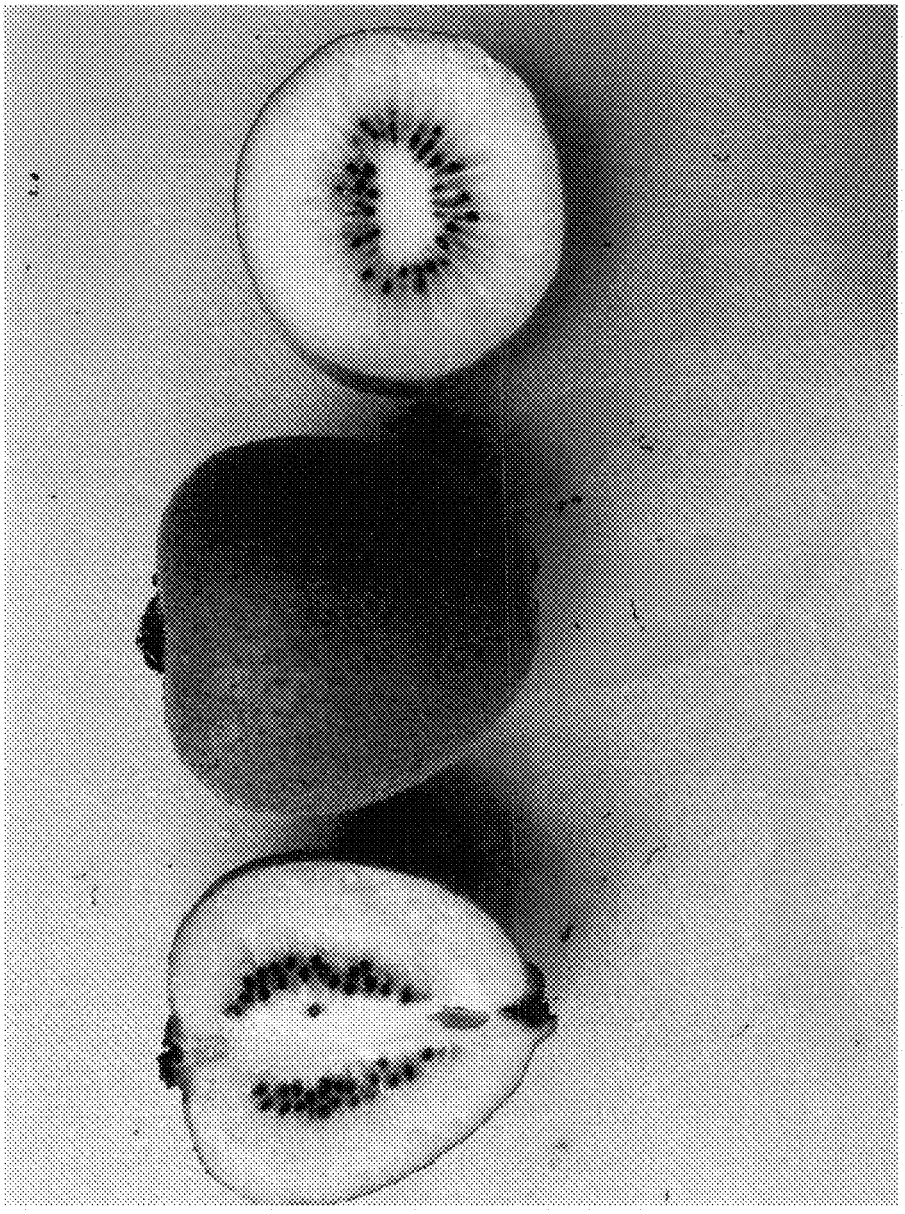
Figure 6E:
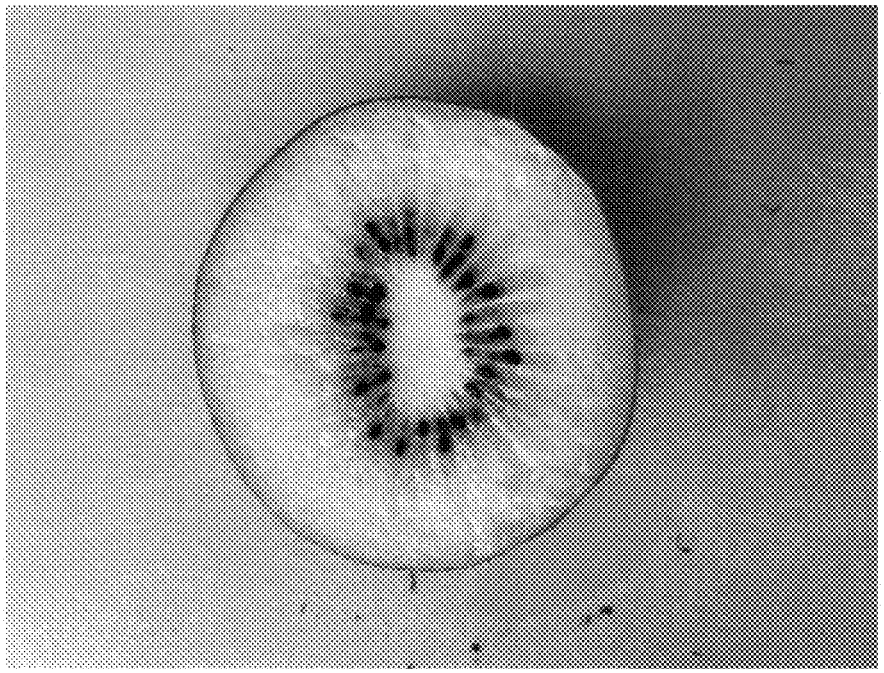
Figure 6D:
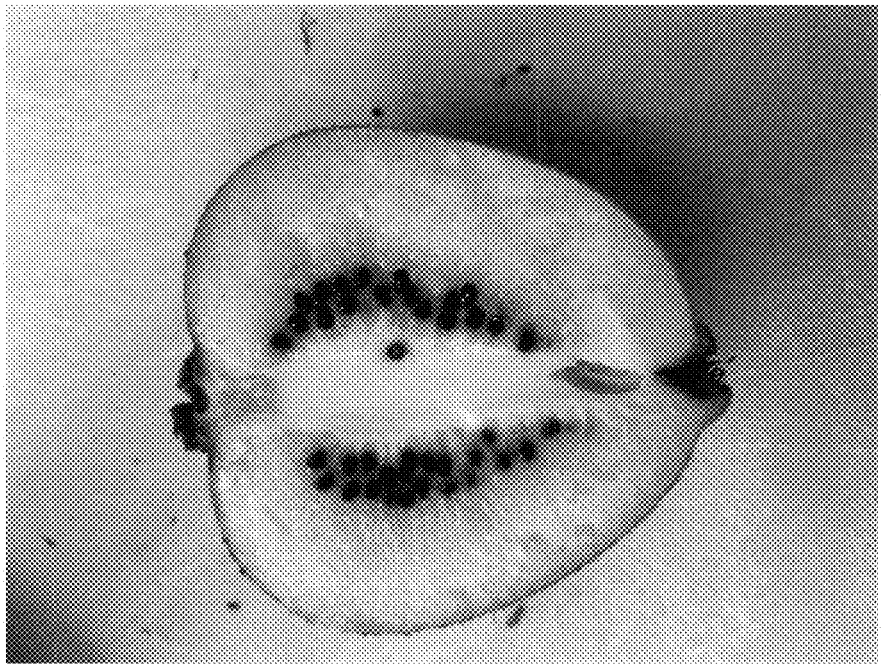
Figure 6F:
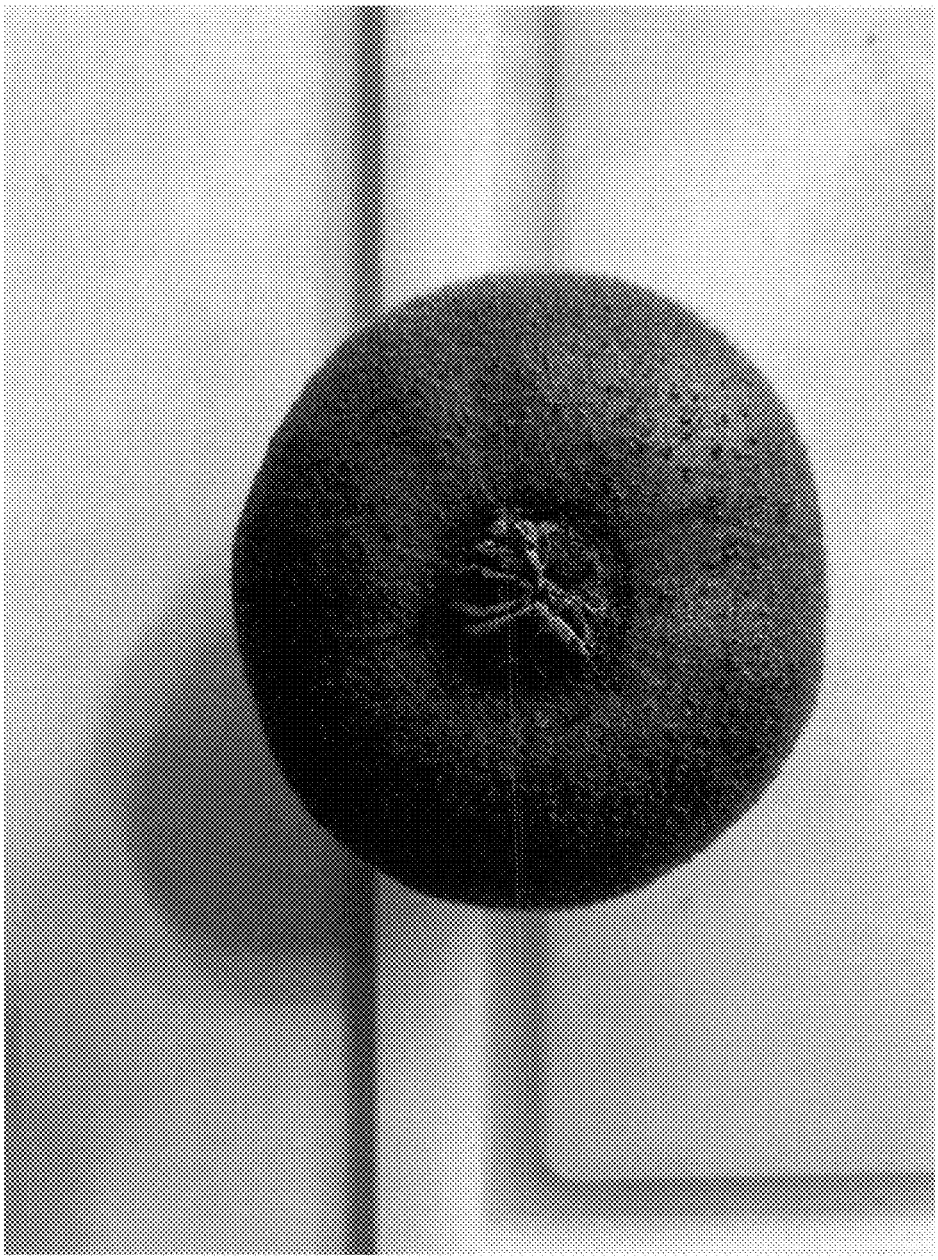

The following detailed descriptions set forth the distinctive characteristics of 'W11'. The data which define these characteristics is based on observations taken in Marysville, CA from 2022-2023. This description is in accordance with UPOV terminology. Color designations, color descriptions, and other phenotypical descriptions may deviate from the stated values and descriptions depending upon variation in environmental, seasonal, climatic, and cultural conditions. 'W11' has not been observed under all possible environmental conditions. The botanical description of 'W11' was taken from plants that were 4-5 years old unless noted otherwise. The indicated values represent averages calculated from measurements of several plants. Color references are primarily to The R.H.S. Colour Chart of The Royal Horticultural Society of London (R.H.S.) (2015 edition).

Classification:
- *Species.*—*Actinidia chinensis.*
- *Common name.*—Gold Kiwi.
- *Denomination.*—W11.

Parentage:
- *Female parent.*—Unknown.
- *Male parent.*—Unknown.

Plant:
- *Sex.*—Female.
- *Use.*—Fresh Fruit.
- *Self-fruit setting.*—Absent.
- *Vigor.*—Medium.

Young shoot:
- *Density of hairs.*—Smooth with very fine tomentose hairs.
- *Anthocyanin coloration of growing tip.*—Absent or very weak.
- *Time of vegetative bud burst.*—Early to late March, about 7-10 days after bud development.

Stem:
- *Length.*—Approximately 1.5-2.5 m.
- *Diameter.*—1.1 cm on average between $5^{th}$ and $6^{th}$ bud.
- *Texture of bark.*—Smooth.
- *Density of hairs.*—Absent.
- *Lenticels.*—Length: 0.25-1.00 mm. Width: 0.05-0.50 mm. Density: 7-10 lenticels per $cm^2$. Color: RHS 148D (Light Brown Green).
- *Buds.*—Length: 0.4-1.0 cm. Width: 0.4-0.7 cm. Shape: Predominately round with straight edges where the petals will emerge. Prominence of bud support: Weak. Presence of bud cover: Absent. Size of hole in bud cover: N/A.
- *Leaf scar.*—Moderately depressed.

Leaf:
- *Ratio of petiole length to blade length.*—1:1.
- *Leaf blade.*—Shape: Orbicular. Length: 13 cm. Width: 15 cm. Ratio of length to width: 13:15. Shape of apex: Emarginate when distal from the shoot apical meristem (where there are between one and four buds developing), closer to the base of the shoot; acuminate when proximal to the shoot apical meristem (where there are three or more buds developing), further from the base of the shoot. Basal lobes: None. Color of upper surface: RHS N134B (Dark Green). Color of lower surface: RHS 134B (Medium Green). Variegation: Absent.
- *Petiole.*—Length: 13 cm. Diameter: 0.25-0.5 cm. Density of pubescence: Medium. Overall color: RHS 149D (Light Green). Anthocyanin coloration of upper side: Absent or very weak.

Inflorescence:
- *Type of inflorescence.*—Solitary.
- *Number of flowers per plant.*—Approximately 2,000.
- *Number of flowers per inflorescence.*—1.
- *Flower bud.*—Overall color: RHS 134D (Light Green). Position of first spike: Low. Number of floral buds per shoot: 4-5, limiting thinning requirements.
- *Flower.*—Flower diameter: Approximately 2-3 cm. Arrangement of petals: Overlapping. Shape in profile: Flat at full maturity. Number of styles: 40-50.Attitude of styles: Erect. Anther color: RHS 151A (Light Green).
- *Petal.*—Number of petals per flower: 6-7. Overall shape: Orbicular. Shape of apex: Rounded.
- *Flowering interval.*—Early to late April.

Fruit:

*Fruit size*.—Length: 53 mm. Width: 52 mm. Length/width ratio: 1:1. Weight: 95-100 g average.

*Shape*.—Cordate.

*Shape in cross section* (*at median*).—Circular.

*Stylar end*.—Weakly protruding with weak depression inside.

*Degree of pointed protrusion*.—Strong.

*Presence of calyx ring*.—Strongly expressed.

*Shape of shoulder at stalk end*.—Truncate.

*Stalk*.—Length: 3.30 cm average. Diameter: 0.25 cm average. Color: RHS 139C (Medium Brown Green).

*Skin*.—Conspicuousness of lenticels on skin: Strong. Hairiness of skin: Present. Density of hairs: Very sparse. Adherence of hairs to skin: Weak. Color of skin (after removal of hair): RHS 146D (Medium Brown Green). Adherence of skin to flesh: Strong.

*Color of outer pericarp*.—RHS 10C (Light Yellow).

*Color of locules*.—RHS 10C (Light Yellow).

*Reddish color along locules*.—Absent.

*Intensity of reddish color in locules*.—Absent.

*Core*.—Diameter: 0.75 cm. General shape of core in cross section: Circular. Color of core: RHS 150D (Light Yellow).

*Sweetness/soluble solids* (*in ° Brix*).—18.

*Mature dry matter, as % of fruit mass retained when dry*.—21-22%.

*Storage characteristics*.—4-6 months at 0° C., allowing shipping and marketing advantageously late in the season.

*Seeds*.—Number per fruit: 600-800.

*Fruiting*.—Market use: Fresh market kiwi fruit (e.g. sold and consumed unprocessed). Harvest interval: Mid-October through November in the Sacramento Valley area of California, U.S.A. Productivity: Estimated 15 tons of fruit per acre (at full maturity). Chilling requirement: Moderate.

COMPARISONS TO REFERENCE KIWI VARIETIES

'W11' differs from the reference variety 'Hayward' (unpatented) in that 'Hayward' has green fleshed fruit with many hairs and low dry matter (~16%), whereas 'W11' has gold fleshed fruit with few hairs and high dry matter (~21-22%). Additionally, the shape of the fruit of 'W11' is heart-shaped, whereas the fruit of 'Hayward' is ovular.

'W11' differs from the reference variety 'Hort16A' (U.S. Plant Pat. No. 11,066) in that. 'W11' has a ripened sweetness of 18° Brix, whereas 'Hort16A' has a sweetness of 15.6° Brix. Additionally, 'W11' has heart-shaped fruit with a stylar end weakly protruding with weak depression inside, whereas 'Hort16A' has ovoid cylindrical fruit with a protruding shape of stylar end.

'W11' differs from the reference variety 'AU Golden Dragon' (U.S. Plant Pat. No. 22,191) in that 'W11' has a higher dry matter percentage (approximately 21-22%), whereas 'AU Golden Dragon' has a lower dry matter percentage (17.2%). Additionally, the fruit of 'W11' is cordate, whereas the fruit of 'AU Golden Dragon' is cylindrical.

'W11' differs from the reference variety 'AU Golden Sunshine' (U.S. Plant Pat. No. 22,159) in that 'W11' has a higher dry matter percentage (approximately 21-22%), whereas 'AU Golden Sunshine' has a lower dry matter percentage (18.5%). Additionally, the fruit of 'W11' is cordate, whereas the fruit of 'AU Golden Sunshine' is elliptical.

We claim:

1. A new and distinct variety of kiwi plant named 'W11' as shown and described herein.

* * * * *